United States Patent
Cheung et al.

(10) Patent No.: US 11,411,297 B1
(45) Date of Patent: Aug. 9, 2022

(54) BURIED WIRELESS UNIT FOR MEASURING AND REPORTING ENVIRONMENTAL PARAMETERS

(71) Applicant: Computime Ltd., New Territories (HK)

(72) Inventors: Kam Tim Cheung, Hong Kong (CN); Wai Yin Shum, Hong Kong (CN)

(73) Assignee: Computime Ltd., New Territories (HK)

( * ) Notice: Subject to any disclaimer, the term of this patent is extended or adjusted under 35 U.S.C. 154(b) by 0 days.

(21) Appl. No.: 17/587,383

(22) Filed: Jan. 28, 2022

Related U.S. Application Data (63) Continuation of application No. 17/458,773, filed on Aug. 27, 2021.

(51) Int. Cl.
| | |
|---|---|
| *H04W 24/08* | (2009.01) |
| *H01Q 1/24* | (2006.01) |
| *H01Q 1/10* | (2006.01) |
| *H04B 1/38* | (2015.01) |
| *G01N 33/24* | (2006.01) |
| *H01Q 1/12* | (2006.01) |
| *H04Q 9/00* | (2006.01) |

(52) U.S. Cl.
CPC .......... *H01Q 1/1235* (2013.01); *G01N 33/24* (2013.01); *H01Q 1/24* (2013.01); *H04Q 9/00* (2013.01); *H04W 24/08* (2013.01); *G01N 2033/245* (2013.01); *H04Q 2209/40* (2013.01)

(58) Field of Classification Search
None
See application file for complete search history.

(56) References Cited

U.S. PATENT DOCUMENTS

| | | | |
|---|---|---|---|
| 5,414,436 A | 5/1995 | Shinkawa et al. | |
| 5,424,649 A | 6/1995 | Gluck et al. | |
| 5,621,669 A | 4/1997 | Bjornsson | |
| 5,689,821 A * | 11/1997 | Shimazaki | H01Q 9/14 343/702 |
| 6,002,975 A | 12/1999 | Schiffmann et al. | |
| 6,191,742 B1 * | 2/2001 | Ha | H01Q 1/362 343/702 |
| 8,031,068 B1 * | 10/2011 | Steadman | G01V 1/223 370/338 |
| 9,532,118 B2 | 12/2016 | Vuran et al. | |
| 10,524,430 B1 * | 1/2020 | Nervino | A01G 25/167 |
| 2008/0199359 A1 | 8/2008 | Davis et al. | |
| 2011/0309274 A1 * | 12/2011 | Parsons | A01G 25/167 251/129.01 |

\* cited by examiner

*Primary Examiner* — Pablo N Tran
(74) *Attorney, Agent, or Firm* — Banner & Witcoff, Ltd.

(57) ABSTRACT

A buried wireless unit measures various soil parameters of surrounding soil and reports them to centralized equipment. In order to provide reliable communication with the centralized equipment, the buried wireless unit may extend a pop-up antenna when transmitting soil parameter data and may subsequently retract the antenna. The wireless unit unwinds and winds a wire, where an electrical cable connects the antenna to a communication module, in order to extend and retract the antenna, respectively. The wireless unit comprises a bendable sleeve enabling the antenna to be flexible so that damage to the wireless unit is avoided if a vehicle (such as a tractor) rolls over the wireless unit. In order to preserve the battery powering the wireless unit, the wireless unit may skip retracting the antenna when the wireless unit determines that charging level of the battery is below a predetermined charging level.

21 Claims, 10 Drawing Sheets

BURIED WIRELESS UNIT FOR MEASURING AND REPORTING ENVIRONMENTAL PARAMETERS

This application claims the benefit of and is a continuation of U.S. patent application Ser. No. 17/458,773, filed Aug. 27, 2021, and entitled "A Buried Wireless Unit for Measuring and Reporting Environmental Parameters," This application is incorporated by reference herein in its entirety.

TECHNICAL FIELD

Aspects of the disclosure relate to measuring and reporting soil parameters by a buried wireless unit.

BACKGROUND OF THE INVENTION

Soil is a complex, living, changing, and dynamic component of the agroecosystem. However, it is subject to alteration, and can be either degraded or wisely managed. A thorough understanding of the ecology of the soil ecosystem is a key part of designing and managing agroecosystems in which the long-term fertility and productive capacity of the soil is maintained or even improved.

Moreover, the properties of soil ecosystems vary both spatially and temporally, even on a small scale. Soil sampling must therefore be carefully planned in order to consider the local variability, where soil monitoring typically entails various types of sampling for different soil properties.

SUMMARY OF THE INVENTION

A buried wireless unit measures various soil parameters of surrounding soil and reports them to centralized equipment. In order to provide reliable communication with the centralized equipment, the buried wireless unit may extend a pop-up antenna when transmitting soil parameter data and may subsequently retract the antenna.

With another aspect, a wireless unit, via one or more sensors, measures soil parameters of the surrounding soil, including, but not limited to, soil moisture, soil temperature, and soil composition.

With another aspect, a motor causes a wire to be unwound from or wound around a wheel, where the wireless connects a pop-up antenna to a communication module. Consequently, the antenna is extended or retracted.

With another aspect, a wireless unit comprises a bendable sleeve enabling the antenna to be flexible so that damage to the wireless unit is avoided if a vehicle rolls over the wireless unit.

With another aspect, a pop-up antenna is affixed to a cap. One or more springs pushes against the cap causing the antenna to extend above ground level as a wire is unwound from a wheel. Conversely, the antenna is retracted when the wire is wound around the wheel overcoming the force applied by the one or more springs against the cap.

With another aspect, a battery powering a wireless unit is preserved by skipping the retraction of a pop-up antenna when the wireless unit determines that the charging level of the battery is below a predetermined charging level.

With another aspect, a predetermined antenna height of a pop-up antenna is adjusted when a wireless unit determines that a measured signal strength is below a predetermined signal strength level. The predetermined antenna height is increased so that reliable communication between the wireless unit and centralized equipment is maintained.

BRIEF DESCRIPTION OF THE DRAWINGS

The foregoing summary of the invention, as well as the following detailed description of exemplary embodiments of the invention, is better understood when read in conjunction with the accompanying drawings, which are included by way of example, and not by way of limitation with regard to the claimed invention.

DETAILED DESCRIPTION

In order to improve agricultural output, knowledge of soil parameters is important. With an aspect of the embodiments, a bendable pop-up antenna of an underground measurement and monitoring unit has a bendable waterproof antenna that can automatically pop up above the ground. When the antenna is popped up, the unit can transmit and receive radio frequency (RF) signals to and from centralized equipment. This approach can achieve reliable long-distance wireless communication with respect to conventional approaches. The antenna is bendable to prevent damage when agricultural machinery roll overs the unit. The unit may also be waterproof to cope with irrigation or rain.

Figure 1:
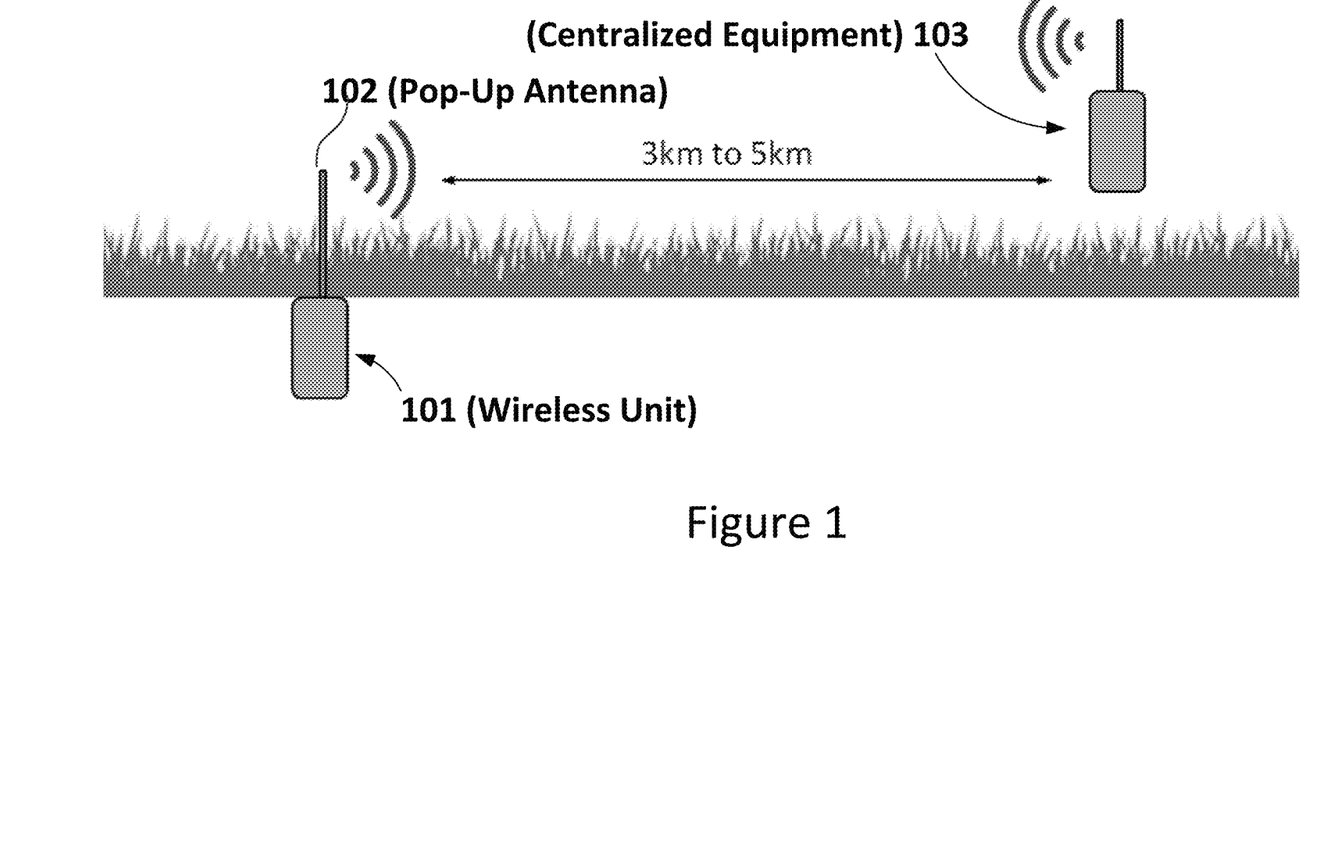
FIG. 1 shows a buried wireless unit communicating with above-ground wireless equipment in accordance with an embodiment.

FIG. 1 shows a buried wireless unit 101 communicating with an above-ground wireless centralized equipment 103 in accordance with an embodiment. For example, wireless unit 101 may be buried in the soil communicating with centralized equipment 103 (such as an above-ground unit and supporting a plurality of buried wireless units) through pop-up antenna 102.

Embodiments may provide a low-cost design and may be used in many applications, such as precision agriculture, environmental monitoring, earthquake monitoring, landslide monitoring, farming, and gardening.

Buried wireless unit 101 may measure various environmental parameters (for example, soil parameters such as soil moisture, soil temperature, and soil composition) in an agricultural application and report them to centralized equipment 103. However, it may be difficult to maintain reliable underground wireless communication with buried devices. Soil type, soil moisture, burial distance depth, and surrounding foliage (for example, crops) often dynamically attenuate the radio frequency (RF) signals.

Soil parameters may be measured by one or more sensors including, but not limited to, cation exchange capacity (CEC), soil organic matter, sodium absorption ratio, soil pH, electrical conductivity.

Above-ground wireless communication typically extends the communication range with respect to configurations where a wireless unit and/or centralized equipment have antennas located below the ground. For example, with LoRa® 433-MHz band underground-to-underground communication at 30 cm burial depth, the maximum transmission distances typically vary from 5 m to 20 m dependent on the type of soil and water content of the soil. (LoRa is a spread spectrum modulation technique derived from chirp spread spectrum technology.) With LoRa 433-MHz band underground-to-aboveground communication at 30 cm burial depth, the maximum transmission distances typically vary from 50 m to 200 m. With LoRa 433-MHz band aboveground-to-aboveground communication (as shown in FIG. 1) with the antenna height of 20 cm above the ground, the maximum transmission distances may reach 3 km to 5 km.

When wireless unit 101 is inserted into the soil, there should be no object positioned above the unit 101, preventing antenna 102 from properly popping up. Also, there should be no large metal objects blocking the radio frequency transmission between pop up antenna 102 and linked centralized equipment.

Figure 2:
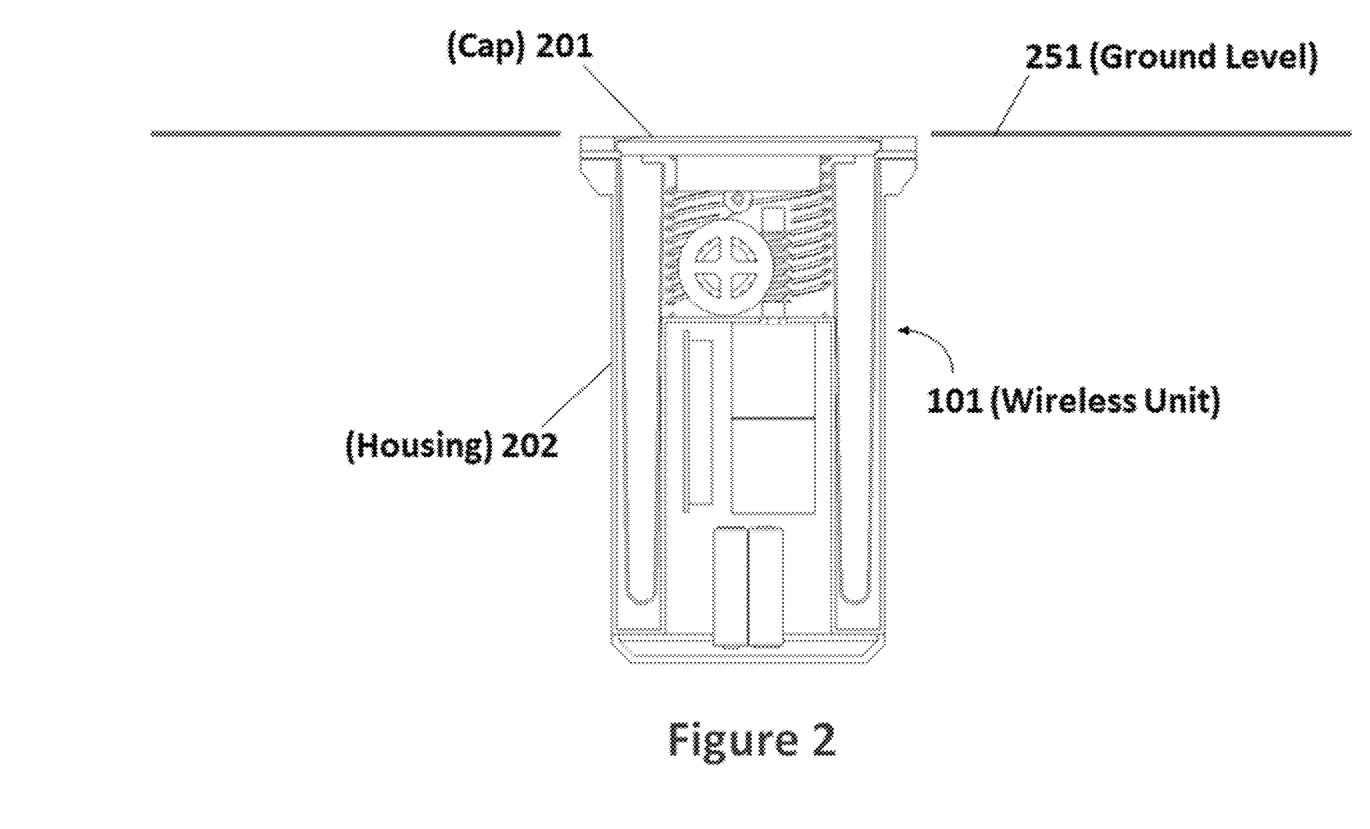
FIG. 2 shows a buried wireless unit in a retracted mode in accordance with an embodiment.

FIG. 2 shows buried wireless unit 101 in a retracted mode, where pop-up antenna 102 is retracted within housing 202 in accordance with an embodiment.

Buried wireless unit 101 is inserted below ground level 251, where cap 201 and housing 202 isolates the components of wireless unit 101 from the surrounding soil. Wireless unit 101 is typically inserted at desired locations for obtaining soil parameters and having reliable wireless communication with centralized equipment.

As will be discussed, wireless unit 101 may be located by centralized equipment. If needed, wireless unit 101 may be extracted by removing the soil, pouring water around unit 101, rotating unit 101, and then pulling it out of the ground.

Figure 3:
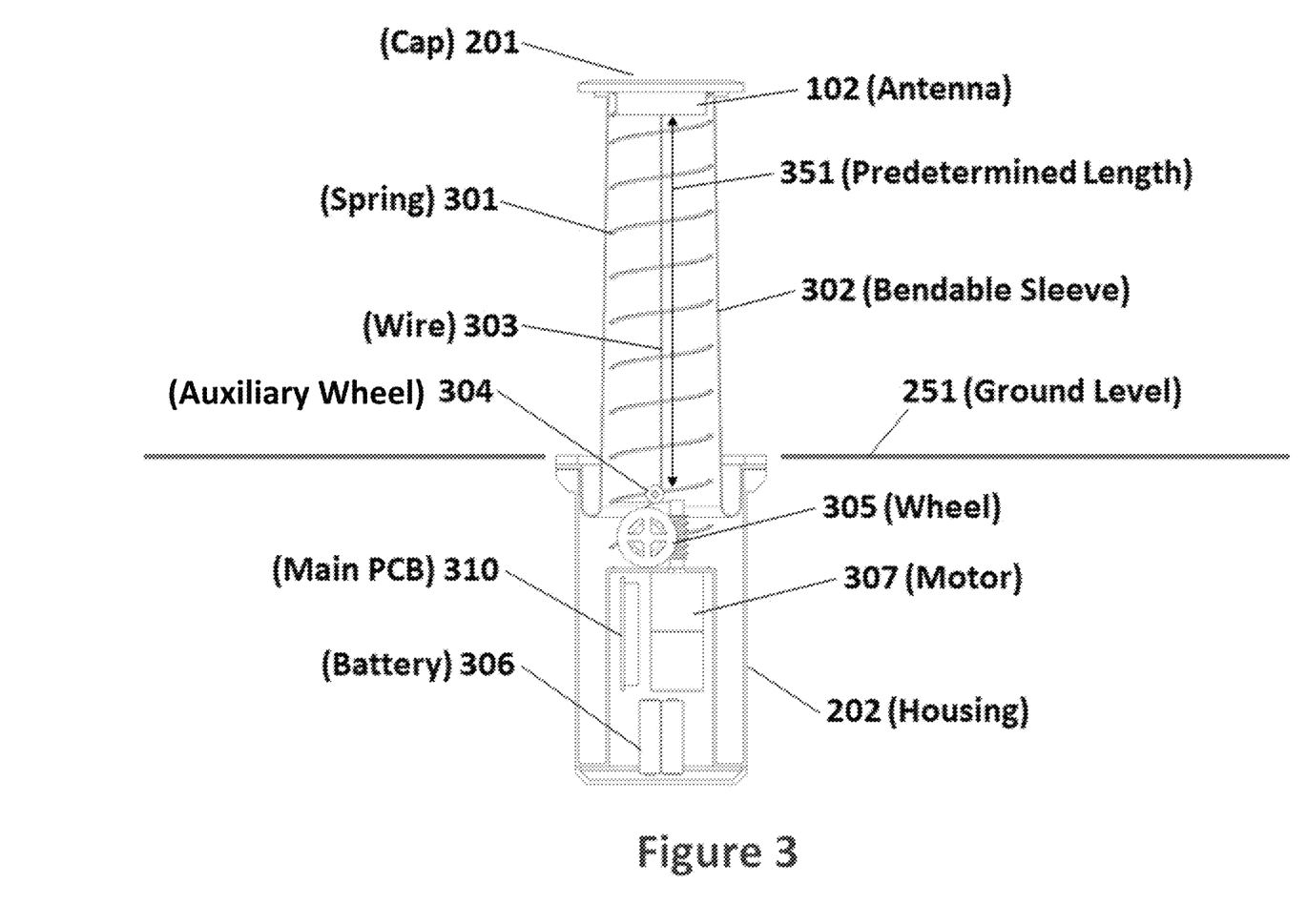
FIG. 3 shows a buried wireless unit in an extended mode in accordance with an embodiment.
Figure 4:
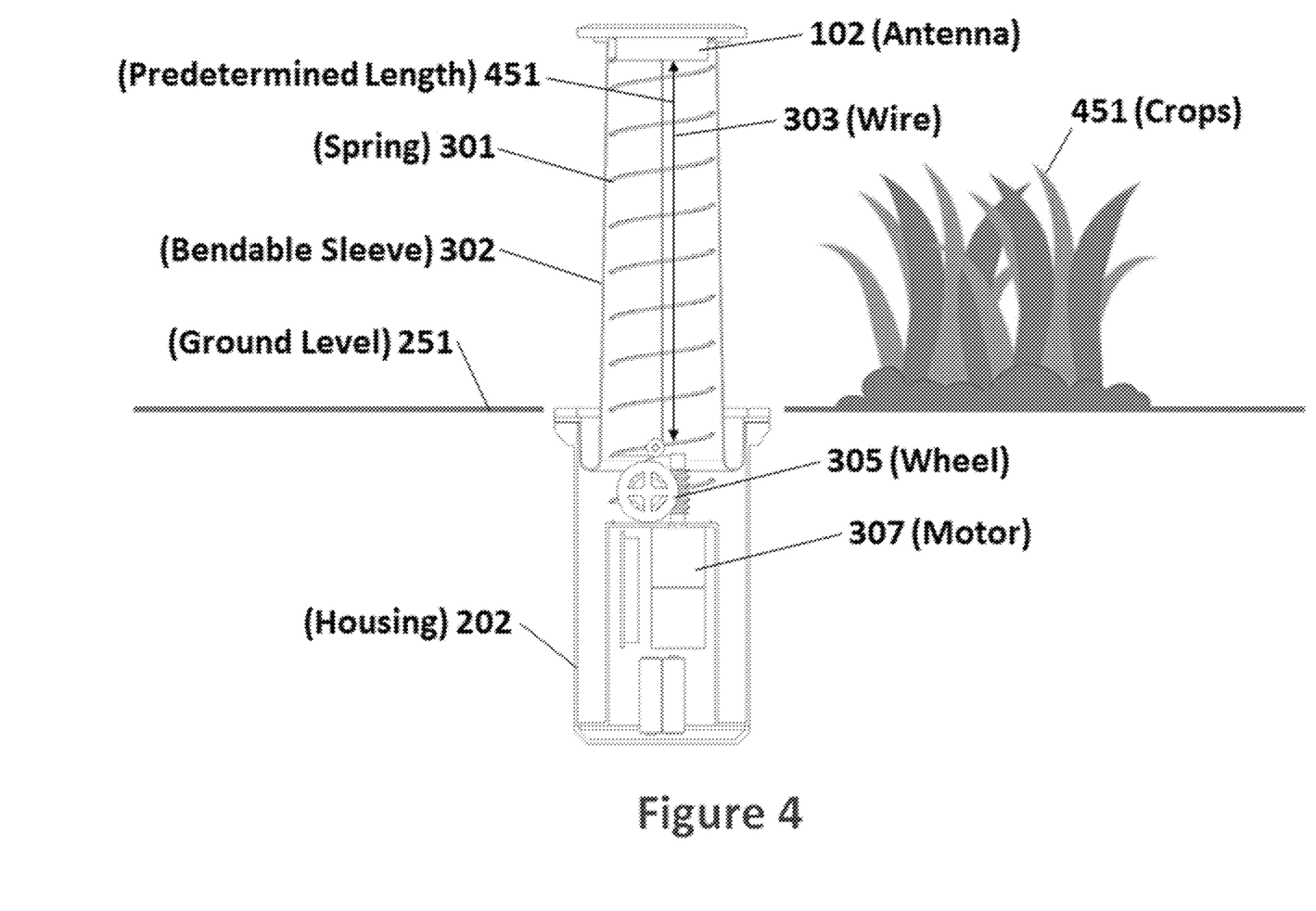
FIG. 4 shows a buried wireless unit in an extended mode in accordance with an embodiment.

FIGS. 3 and 4 show buried wireless unit 101 in an extended mode in accordance with an embodiment. FIGS. 3 and 4 are similar, but predetermined lengths 351 and 451 corresponding to the heights of antenna 102 as shown in FIGS. 3 and 4, respectively, are different to address the effects of crops (foliage) 451 upon the communication channel between unit 101 and centralized equipment. For example, FIG. 3 may correspond to an early part of a growing season (for example, just after planting crops) while FIG. 4 may correspond to a later part of the growing (for example, just before harvesting).

Referring to FIG. 3, buried unit 101 is buried below ground level 251. In order for buried unit 101 to communicate with centralized equipment (for example, a gateway), antenna 102 is extended predetermined distance 351 by motor 307 unwinding wire 303 that is wrapped around wheel 305. As wire 303 is unwound by predetermined distance 351, spring 301 pushes against cap 201 causing cap 201 to raise predetermined distance 351. Because antenna 102 is affixed to cap 201, antenna 102 also raises predetermined distance 351.

Some embodiments may utilize different forms of a rotational object other than wheel 305. A rotation object may include, but is not limited to, a cylinder and a pully.

Bendable sleeve 302 is bonded to cap 201 and housing 202 and thus provides a barrier to environmental elements such as rain and wind. Bendable sleeve 302, for example, may be constructed from silicon rubber. In addition, bendable sleeve 302 is bendable so that is a vehicle (for example, a tractor rolling over buried unit 101) or a person (stepping on buried unit 101) does not damage buried unit 101, and thus unit 101 can continue normal operation. Bendable sleeve 302 unfolds from housing 202 to accommodate extending antenna 102 as wire 303 is unwound from wheel 305 by motor 307. Conversely, bendable sleeve 302 folds into housing 202 as wire 303 is wound onto wheel 305 in order to retract antenna 102 into housing 202.

With some embodiments, antenna 102 may be in one of two positions: either in a retracted position, where antenna 102 is retracted into housing 202 with cap 102 at ground level 251, or in an extended position, where antenna 102 is extended to a predetermined height (corresponding to predetermined length 351).

Figure 3A:
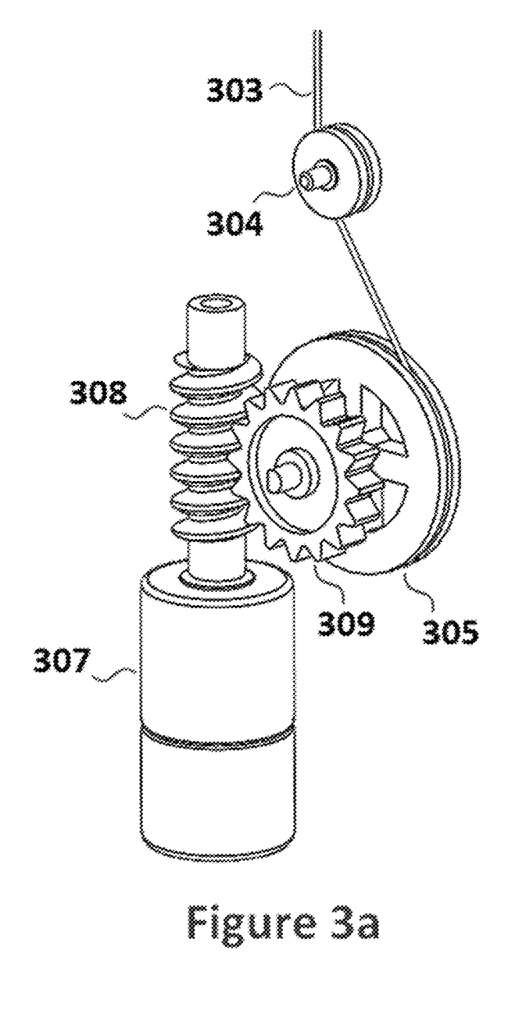
FIG. 3a shows a wire of a buried wireless unit that is wound/unwound around a wheel in accordance with an embodiment.
Figure 3B:
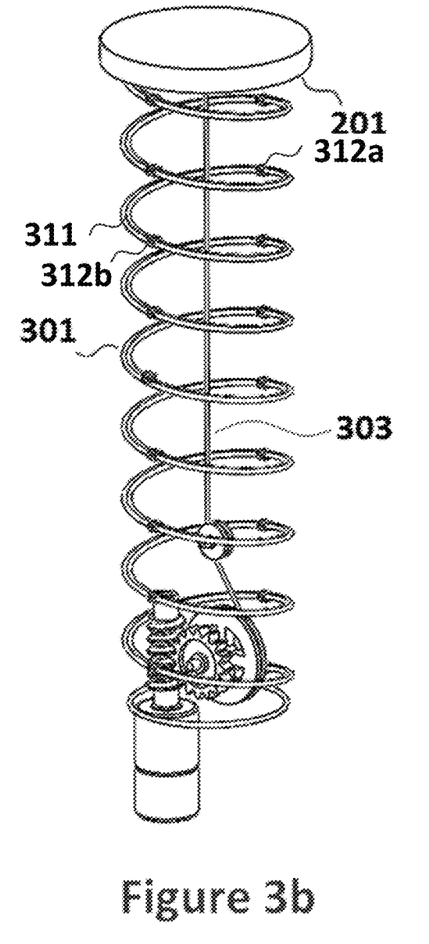
FIG. 3b shows an electrical cable of a buried wireless unit that is clipped on a spring in accordance with an embodiment.
Figure 6:
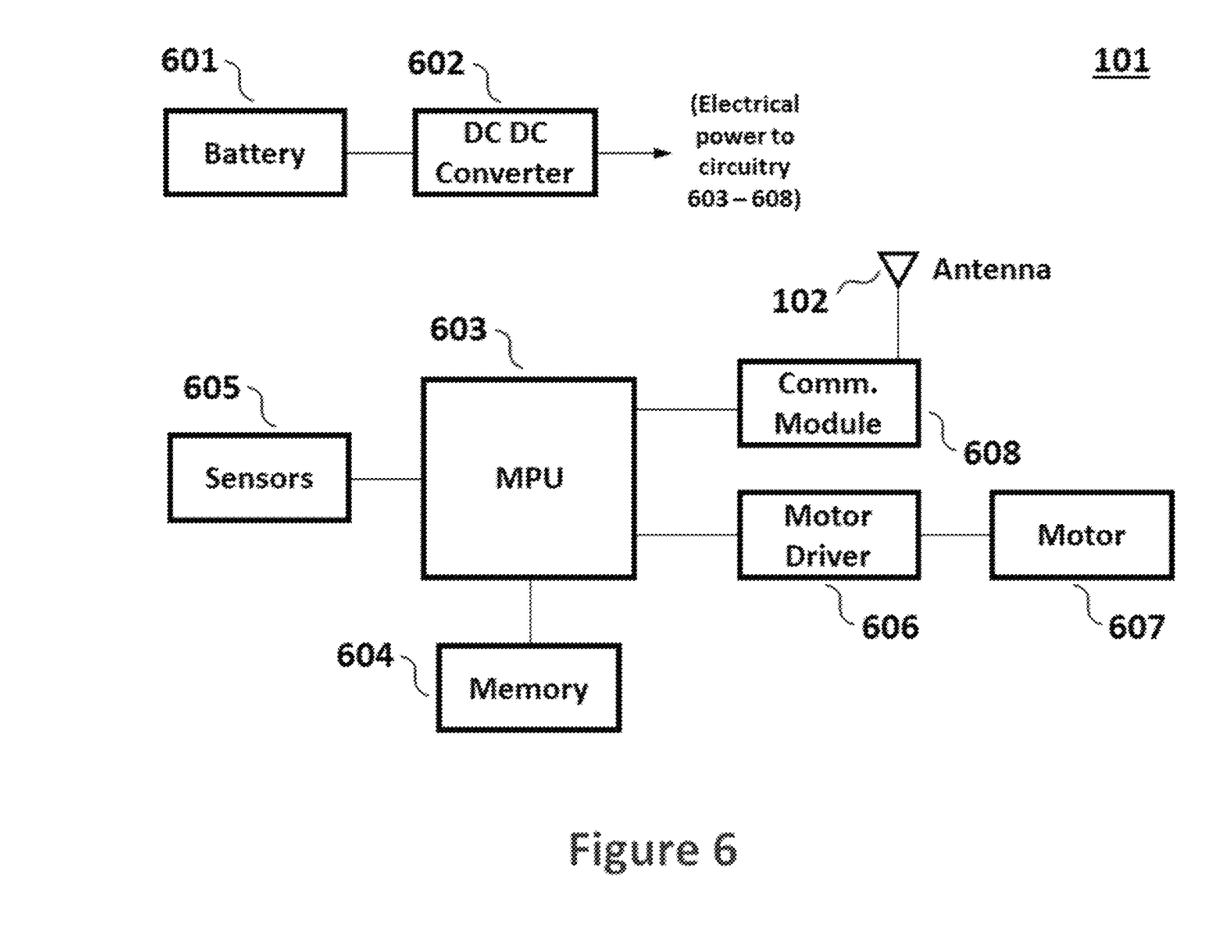
FIG. 6 shows a wireless unit that may be buried in soil in accordance with an embodiment.

In addition to restraining movement of antenna 102 by wire 303, electrical cable 311 (as shown in FIG. 3b) is used to connect electrical circuit (for example, communication module 608 as shown in FIG. 6) to antenna 102. Communication module 608 may transmit and/or receive a signal by supporting one of different radio techniques including, but not limited to, LoRa, Wi-Fi, and 5G wireless technologies. FIG. 3a shows wire 303 being wound/unwound on the wheel 305. Motor 307 is coupled to worm gear 308 to link with spur gear 309 and wheel 305, thus driving cap 201 up or down. Wire 303 is wound around wheel 305. Auxiliary wheel 304 may be used to position wire 303 to the center of wireless unit 101.

Battery 306 provides electrical power to motor 307 as well as to electrical circuitry (not explicitly shown) as will be discussed in greater detail.

Referring to FIG. 3b, spring 301 is used to provide upward force and push the cap 201 above the ground level, where wire 303 is guided through the interior of spring 301. Antenna 102 may be installed beneath cap 201 and may be connected to communication module 608 (which may support LoRa circuitry) on main PCB 310 via electrical cable 311. Cable 311 may be clipped on spring 301 with a plurality of clips (such as clips 312a,b) and routed along with spring 301 conforming to a spiral shape.

Referring to FIG. 4, foliage (for example, crops 451) may grow above ground level 251 throughout a growing season. Consequently, antenna 102 may be extended to a greater height to compensate for the increased foliage height. In order to accommodate the increased antenna height, the predetermined length may be adjusted (increased) to predetermined length 451 (with respect to predetermined length 351) so that additional wire 303 may be unwound from wheel 305 by motor 307. Consequently, spring 301 pushes antenna 102 to a higher height as bendable sleeve 302 unfolds from housing 202.

Figure 5:
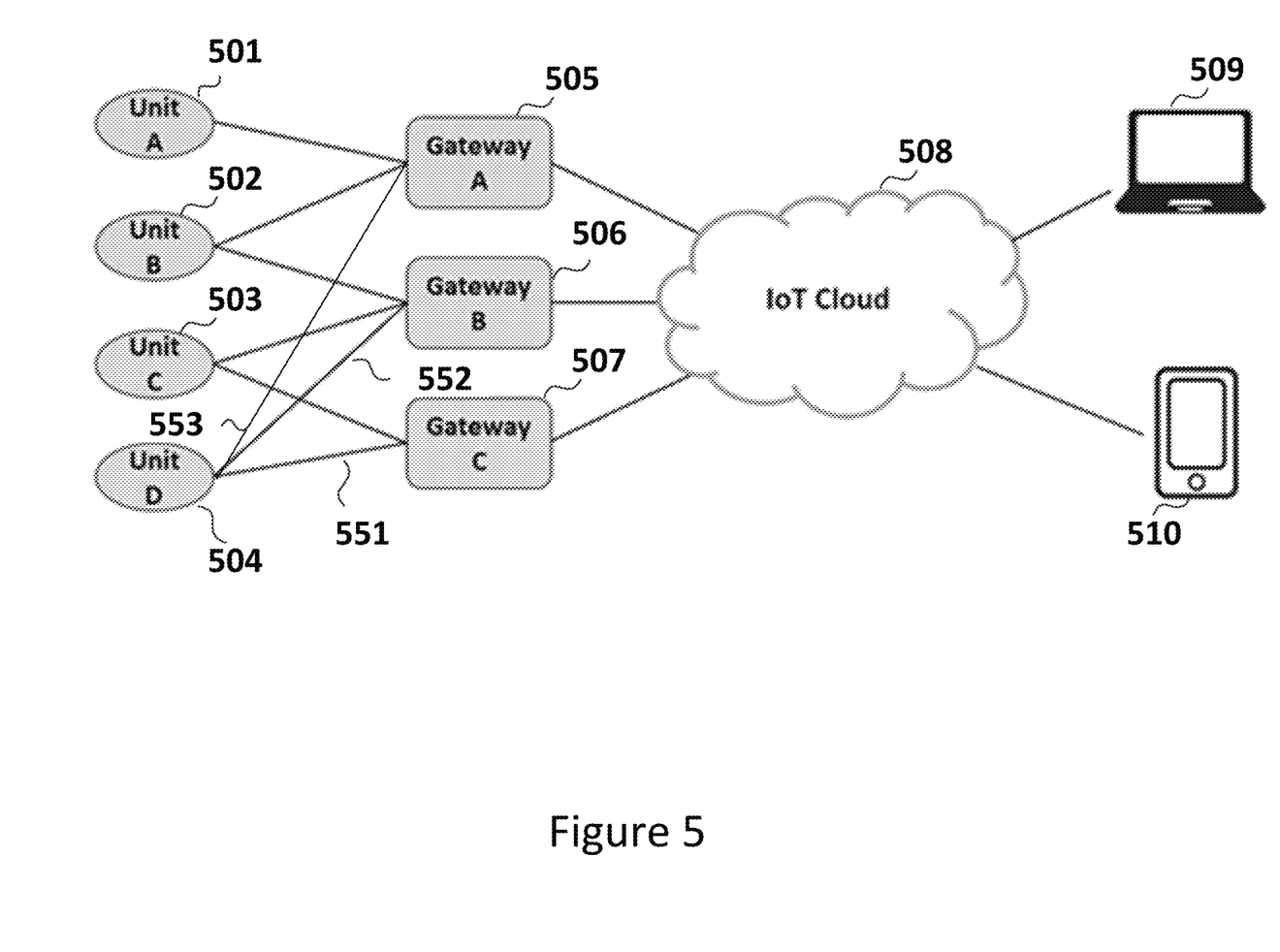
FIG. 5 shows a plurality of wireless units configured in a communication network in accordance with an embodiment.

FIG. 5 shows a plurality of wireless units 501-504 configured in a communication network in accordance with an embodiment. Wireless units 501-504 communicate with gateways 505-507 via wireless communication channels (links) such as channels 551-553.

Wireless units 501-504 may communicate with one or more gateways 505-507 through a long-range star topology network utilizing LoRa technology. Gateways 505-507 are typically installed above ground level 251. A wireless unit 501-504 extends (pop ups) its antenna above ground level 251 to send and receive data through the gateways.

Wireless units 501-504 may be located by three or more gateways (for example, unit 504 by gateways 505-507). To locate a wireless unit, one or more radio signal measurements may be performed between the unit and the gateways.

For example, gateways 505-507 obtain the information that characterize the spatial relationship between a unit and each gateway. Typical measurements may include the Received Signal Strength Indication (RSSI), Signal to Noise Ratio (SNR), Frequency Offset, Angle of Arrival (AOA), and Time of Arrival (TOA). Based on some or all of these measurements, along with the known positions of the gateways, the predicted position of a unit may be calculated. Once a unit is determined, the unit may be serviced (such as replacing the battery of the unit) or may be extracted from the soil.

Gateways 505-507 may be further linked to a network (such as cloud 508) in order to provide communication connectivity between computing devices 509 and/or 510 and wireless units 501-504 via gateways 505-507. For example, measured soil parameters and the positions of units 501-504 may be displayed on computing devices 509 and/or 510.

Cloud 508 may comprise a platform that is designed to store and process Internet of Things (IoT) data.

FIG. 6 shows wireless unit 101 that may be buried in soil in accordance with an embodiment.

Figure 7:
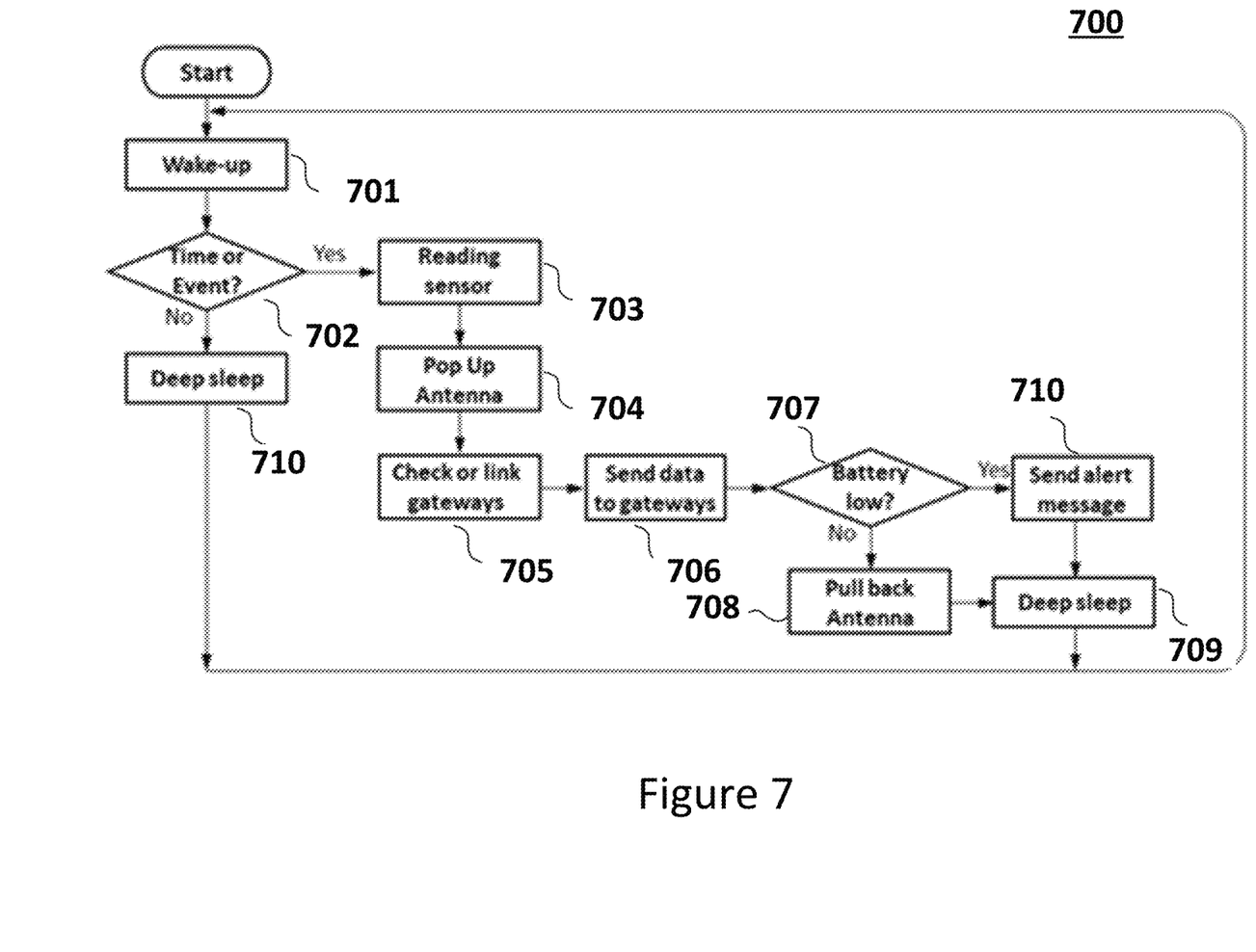
FIGS. 7-8 show flowcharts that may be executed by processing circuitry of a wireless unit in accordance with an embodiment.

A processing device (for example, microprocessor unit (MPU 603)) may execute predefined tasks according to process 700 (as shown in FIG. 7) in order to receive measurement data from sensors 605, control pop-up antenna 102 via motor driver 606 and motor 607, and communicate with units 501-504 via communication circuit (module) 608.

With some embodiments, antenna 102 and communication module 608 may be installed together beneath the cap 201. Cable 311 may be clipped on spring 301 and may include a plurality of conductors. For example, cable 311 may electrically connect a LoRa communication module (not explicitly shown) from cap 201 to main PCB 310.

Processing device 603 may measure, but not limited to, the soil moisture, soil PH value, or any environmental parameters via sensors 605.

Processing device 603 controls operation of wireless unit 101 by executing computer readable instructions stored on memory device 604. For example, processing device 603 may execute computer readable instructions to perform process 700 as will be discussed with FIG. 7. Embodiments may support a variety of computer readable media that may be any available media accessed by processing device 603 and include both volatile and nonvolatile media and removable and non-removable media. By way of example, and not limitation, computer readable media may comprise a combination of computer storage media and communication media.

Computer storage media may include volatile and nonvolatile, removable and non-removable media implemented in any method or technology for storage of information such as computer readable instructions, data structures, program modules or other data. Computer storage media include, but is not limited to, random access memory (RAM), read only memory (ROM), electronically erasable programmable read only memory (EEPROM), flash memory or other memory technology, CD-ROM, digital versatile disks (DVD) or other optical disk storage, magnetic cassettes, magnetic tape, magnetic disk storage or other magnetic storage devices, or any other medium that can be used to store the desired information and that can be accessed by the processing device.

Communication media typically embodies computer readable instructions, data structures, program modules or other data in a modulated data signal such as a carrier wave or other transport mechanism and includes any information delivery media. Modulated data signal is a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

Processing device 603 may be implemented in a number of ways. For example, processing device 603 may be implemented with a microcontroller that typically includes a central processing unit (CPU), in addition with a fixed amount of RAM, ROM and other peripherals all embedded on a single chip. However, processing circuitry may be implemented with a plurality of integrated circuits and/or discrete electronic components.

Battery 601, via DC-DC converter 602, provides electrical power to electrical circuitry 603-608, where DC-DC converter 602 provides the proper regulated voltage levels.

FIG. 7 shows flowchart 700 that is executed by processing device 603 in order for wireless unit 101 to measure soil parameters and reporting them to computing devices 509 and/or 510.

In order to conserve battery life of battery 601, wireless unit 101 operates in the deep sleep mode but wakes up periodically at block 701 to determine if a designated event occurs at block 702. For example, there may be battery low interrupt event, which may wake up processing device 603. Processing device 603 may then generate an alert message to the user to remind the user about changing battery 601. With another example, sensors 605 may detect rain, causing processor device 603 to wake up and to send measurement data to IoT cloud 508. If a designated event is not detected, wireless unit 101 may return into the deep sleep mode until the next cycle time.

If a designated event (for example, a designated time) is detected at block 702, processing device 603 obtains one or more soil parameters from sensors 605 at block 703. In order to report the measured soil parameters to one or more linked gateways, at block 704 processing device instructs motor 607, via motor driver 606, to unwind wire 303 so that antenna 102 is positioned at a predetermined height (in other words, antenna 102 pops up).

At block 705, processing device 603 verifies that communication is properly established with the associated gateways in order to send (transmit) soil parameter data to the gateways at block 706 via communication module 608 and antenna 102.

When transmission of the soil parameter data has been completed, processing device 603 determines whether the battery charge is above a predetermined level at block 707. If so, processing device 603 retracts (pulls back) antenna 102 into housing 202 at block 708. Otherwise, antenna 102 remains in the extended position so that battery 601 conserves its electrical power while being able to provide power to module 608 for subsequent communication. However, as discussed previously, sleeve 302 is bendable (flexible) so that the protruded portion of wireless unit 101 is not damaged if a vehicle rolls over antenna 102. Also, at block 710 wireless unit 101 sends an alert message to the user at devices 509/510 via associated gateways 501-504 and network (cloud) 508, where the message is indicative that the battery needs to be replaced.

With some embodiments, as with process 700 as discussed above, wireless unit 101 transmits data to associated gateways. Moreover, wireless unit 101 may receive commands and/or data from the associated gateways. For example, one or more gateways may send a request to a wireless unit to schedule soil parameter reporting on single or periodic basis.

After executing blocks 708 or 709, wireless unit 101 returns to the deep sleep mode until the next cycle in order to conserve the charging level of battery 601.

Figure 8:
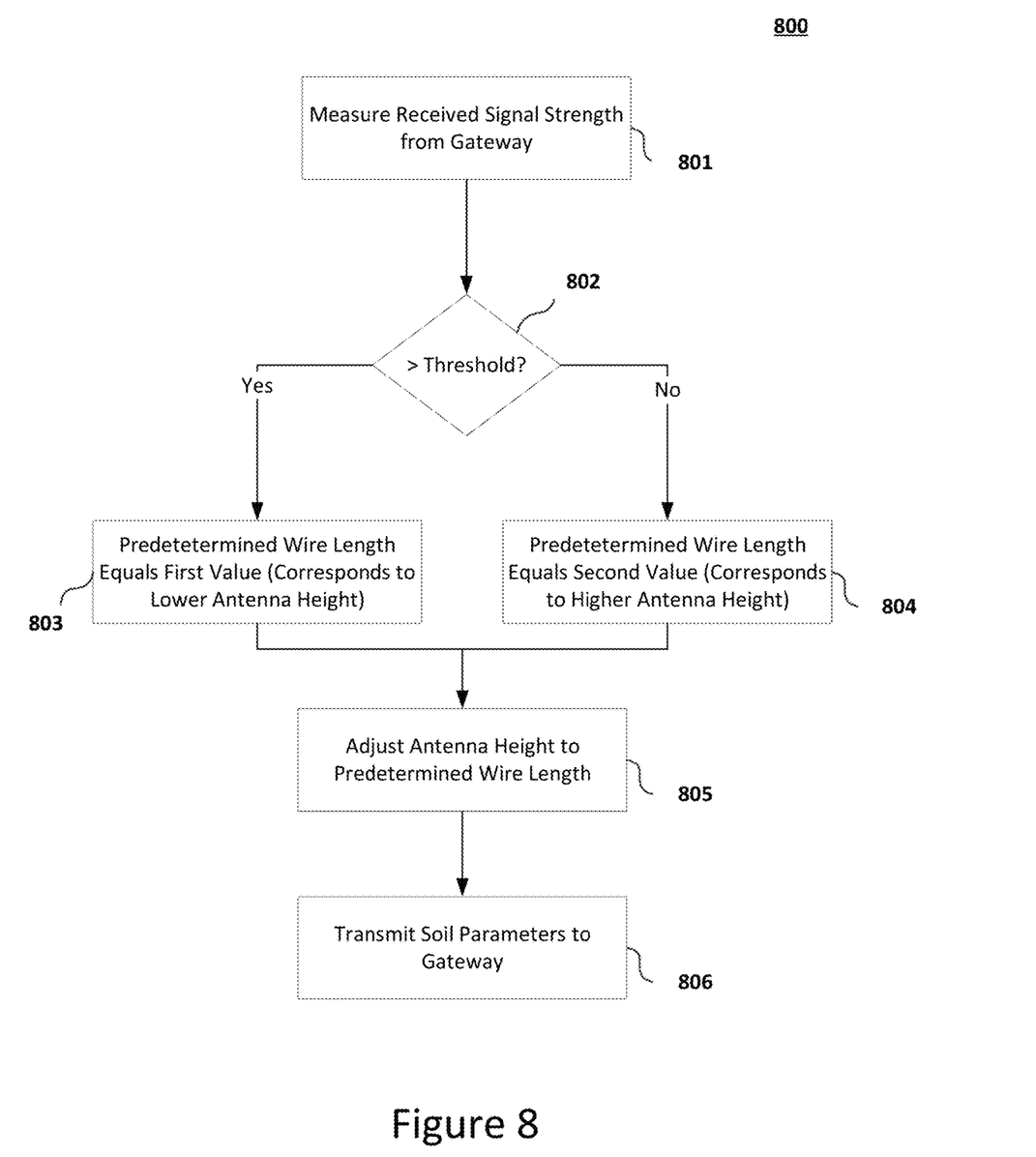

FIG. 8 shows flowchart 800 that is executed by processing device 603 in order for wireless unit 101 to measure the signal strength of a signal from one or more associated gateways and to consequently determine whether the predetermined height (corresponding to the predetermined length of wire 303) of antenna 102 (when popped up) needs to be adjusted.

At block 801, wireless unit 101 measures the signal strength of the received signal from the associated gateway. If the measured signal strength is below a predetermined threshold corresponding to block 802, the received signal should be increased at block 804 for reliable communication. Consequently, the predetermined length of wire 303 may be increased (if wire 303 and bendable sleeve 302 can accommodate the increase) so that the antenna height of antenna 102 is increased when extended. Otherwise, at block 803 the predetermined length of wire 303 remains the unchanged so the antenna height remains the same.

While the antenna height is adjusted based on the signal strength of the received signal at wireless unit 101, some embodiments may measure the signal strength of the received signal at the gateway (assuming channel reciprocity). The gateway can then send a subsequent message to wireless unit 101 to adjust the antenna height.

Various aspects described herein may be embodied as a method, an apparatus, or as computer-executable instructions stored on one or more non-transitory and/or tangible computer-readable media. Accordingly, those aspects may take the form of an entirely hardware embodiment, an entirely software embodiment (which may or may not include firmware) stored on one or more non-transitory and/or tangible computer-readable media, or an embodiment combining software and hardware aspects. Any and/or all of the method steps described herein may be embodied in computer-executable instructions stored on a computer-readable medium, such as a non-transitory and/or tangible computer readable medium and/or a computer readable storage medium. Additionally or alternatively, any and/or all of the method steps described herein may be embodied in computer-readable instructions stored in the memory and/or other non-transitory and/or tangible storage medium of an apparatus that includes one or more processors, such that the apparatus is caused to perform such method steps when the one or more processors execute the computer-readable instructions. In addition, various signals representing data or events as described herein may be transferred between a source and a destination in the form of light and/or electromagnetic waves traveling through signal-conducting media such as metal wires, optical fibers, and/or wireless transmission media (e.g., air and/or space).

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the disclosure.

What is claimed is:

1. A wireless unit for measuring and reporting at least one environmental parameter when the wireless unit is buried in soil, the wireless unit comprising:

an antenna;
a communication circuit configured to support a wireless channel for conveying the at least one environmental parameter through the antenna;
an electrical cable connecting the antenna to the communication circuit;
a wire; and
an adjustment mechanism configured to wind the wire to vary a height of the antenna, wherein the antenna is adjustable from a retracted position below the soil to an extended position above the soil.

2. The wireless unit of claim 1, further comprising:
a cap attached to the antenna; and
at least one spring pushing against the cap, wherein movement of the cap is constrained by the wire.

3. The wireless unit of claim 2, further comprising:
a housing accommodating the communication circuit and the adjustment mechanism; and
an expandable sleeve encompassing the antenna, wherein the expandable sleeve is attached to the cap and the housing.

4. The wireless unit of claim 3, wherein the expandable sleeve is bendable.

5. The wireless unit of claim 3, wherein the expandable sleeve is waterproof.

6. The wireless unit of claim 1, wherein the adjustment mechanism comprises a motor configured to control the winding of the wire.

7. The wireless unit of claim 6, wherein the adjustment mechanism comprises a circular object, wherein the motor causes movement of the circular object to unwind the wire around the circular object in order for the antenna to be in the extended position above the soil.

8. The wireless unit of claim 7, wherein the motor controls the movement of the circular object to wind the wire around the circular object in order for the antenna to be in the retracted position below the soil.

9. The wireless unit of claim 8, further comprising:
a first sensor configured to obtain first information about a first environmental parameter.

10. The wireless unit of claim 9, further comprising:
a processing circuit configured to convey the first information about the first environmental parameter over the wireless channel through the communication circuit and the antenna.

11. The wireless unit of claim 10, further comprising:
a motor driver configured to control the motor to wrap the wire around the circular object; and
the processing circuit configured to instruct the motor driver to adjust a length of the wire to equal a predetermined wire length.

12. The wireless unit of claim 11, wherein the processing circuit is configured to instruct the motor driver so that the antenna is in the extended position above the soil when a detected event is occurs, wherein the extended position corresponds to the predetermined wire length.

13. The wireless unit of claim 11, wherein the processing circuit is configured to instruct the motor driver so that the antenna is in the retracted position below the soil when data transmission has been completed.

14. The wireless unit of claim 11, wherein the processing circuit is configured to instruct the motor driver so that the antenna is in the retracted position below the soil when data transmission has been completed and when a battery is above a predetermined charging level.

15. The wireless unit of claim 14, wherein the antenna remains in the extended position when the battery is not above a predetermined charging level.

16. The wireless unit of claim 11, wherein the processing circuit is configured select the predetermined wire length from one of a first value and a second value.

17. The wireless unit of claim 2, wherein the electrical cable is attached to the at least one spring.

18. A method for obtaining at least one soil parameter by a wireless unit, wherein the wireless unit is buried in soil below, the method comprising:
   detecting an occurrence of a designated event;
   in response to the detecting, obtain soil parameter information from at least one sensor;
   unwinding a wire within the wireless unit by a predetermined length to extend an antenna of the wireless unit above a ground level of the soil at a predetermined height;
   transmitting the soil parameter information over a wireless channel to centralized communication equipment; and
   determining, after the transmission and based on a criterion, whether to retract the antenna below the ground level.

19. The method of claim 18, wherein the determining comprises:
   measuring a charging level of a battery providing electrical power to the wireless unit:
   when the charging level is at least a predetermined charging level, retracting the antenna; and
   when the charging level is below the predetermined charging level, maintaining the antenna at the predetermined antenna height.

20. The method of claim 18, wherein the determining comprises:
   measuring a signal strength of a received signal from the centralized communication equipment; and
   when the measured signal strength is below a predetermined signal strength level, adjusting the predetermined length to increase the predetermined antenna height.

21. One or more non-transitory computer-readable media storing instructions that, when executed by a buried wireless unit at least one processor, memory, and a sensor, cause the buried wireless unit to:
   detect an occurrence of a designated event;
   when the designated event is detected, obtain soil parameter information of soil from the sensor;
   instruct a motor to unwind a wire within the buried wireless unit by a predetermined length to extend an antenna of the buried wireless unit above a ground level of the soil at a predetermined height;
   transmit the soil parameter information over a wireless channel to centralized communication equipment;
   measuring a charging level of a battery providing electrical power to the buried wireless unit:
   when the charging level is at least a predetermined charging level, instruct the motor to wind the wire by the predetermined length to retract the antenna; and
   when the charging level is below the predetermined charging level, maintaining the antenna at the predetermined height.

* * * * *